United States Patent
Rae et al.

(10) Patent No.: US 6,365,604 B1
(45) Date of Patent: Apr. 2, 2002

(54) ANTIPSYCHOTIC SUBSTITUTED PIPERIDINE DERIVATIVES

(75) Inventors: Duncan Robertson Rae, Lanark; David Robert Jaap, Cumbernauld, both of (GB)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/529,204

(22) PCT Filed: Oct. 7, 1998

(86) PCT No.: PCT/EP98/06521

§ 371 Date: Jun. 1, 2000

§ 102(e) Date: Jun. 1, 2000

(87) PCT Pub. No.: WO99/19324

PCT Pub. Date: Apr. 22, 1999

(30) Foreign Application Priority Data

Oct. 7, 1997 (EP) .............................. 97203107

(51) Int. Cl.[7] .................. A61K 31/4535; A61K 31/454; C07D 401/06; C07D 409/14; C07D 401/14
(52) U.S. Cl. .................. 514/326; 514/333; 546/208; 546/212
(58) Field of Search .................. 546/187, 207, 546/212, 208; 514/318, 320, 326, 333

(56) References Cited

U.S. PATENT DOCUMENTS

| 2,739,968 A | | 3/1956 | Sperber et al. |
| 4,540,780 A | | 9/1985 | Downs et al. |
| 4,640,925 A | * | 2/1987 | Downs et al. ............... 514/331 |
| 5,935,974 A | * | 8/1999 | Rae et al. ................... 514/326 |

FOREIGN PATENT DOCUMENTS

| EP | 0 463 873 | 1/1992 |
| WO | WO 97/03065 | 1/1997 |

* cited by examiner

Primary Examiner—Alan L. Rotman
Assistant Examiner—Rita Desai
(74) Attorney, Agent, or Firm—William H. Blackstone

(57) ABSTRACT

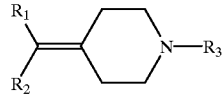

The present invention relates to certain novel substituted piperidine derivatives of formula (I) to processes for their preparation, to pharmaceutical formulations containing them and to their use in medical therapy, particularly in the treatment of psychotic disorders.

9 Claims, No Drawings

ANTIPSYCHOTIC SUBSTITUTED PIPERIDINE DERIVATIVES

CROSS-REFERENCE

This application is a 371 of PCT/EP98/06521 filed Oct. 7, 1998.

The present invention relates to certain novel substituted piperidine derivatives, to processes for their preparation, to pharmaceutical formulations containing them and to their use in medical therapy, particularly in the treatment of psychotic disorders.

U.S. Pat. No. 2,739,968 describes substituted piperidine derivatives having antihistaminic, antispasmodic, antiacetylcholine and analgesic activity. U.S. Pat. Nos. 4,666,905 and 4,540,780 describe diphenylmethylene derivatives which are useful as antiemetic, antihistamine, pulmonary antispasmodic agents.

Effective antipsychotic (neuroleptic) agents include tricyclic phenothiazines, thioxanthenes and dibenzepines as well as benzamides and butyrophenones. These compounds block dopamine D2 receptors and inactivate dopamine transmission. As a result of this, these compounds induce characteristic neurological side effects in man such as extrapyramidal side effects e.g. dystonia and dyskinesia (R. J. Baldessarini, 1996, Goodman and Gilman's The Pharmacological Basis of Therapeutics 9th ed., eds J. G. Hardman et. al.). In animal tests such side effects manifest themselves as catalepsy. It would be advantageous therefore to provide a series of antipsychotic agents which do not have these debilitating side effects.

The present invention provides certain substituted piperidine derivatives which have potent antipsychotic activity but exhibit minimal or no cataleptic effects, and thus would not induce extrapyramidal side effects in the therapeutic dose range.

Thus, according to one aspect, the present invention provides the compounds of formula (I)

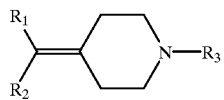

(I)

wherein
- $R_1$ is benzothienyl, benzofuranyl, naphthyl (where the benzothienyl, benzofuranyl or naphthyl moiety may be optionally substituted by one or more substituents selected from halogen, $C_{1-6}$alkyl, $C_{3-6}$cycloalkyl, $C_{1-6}$alkoxy and $C_{2-6}$alkenyl), substituted-thienyl or substituted-furanyl (where the thienyl or furanyl moiety is substituted by one or more substituents selected from halogen, $C_{1-6}$alkyl, $C_{3-6}$cycloalkyl, $C_{1-6}$alkoxy and $C_{2-6}$alkenyl);
- $R_2$ is substituted-phenyl or substituted-thienyl (where the phenyl or thienyl moiety is substituted by one or more substituents selected from $C_{1-6}$alkyl and halogen);
- $R_3$ is —$(CH_2)_m XCONR_4R_5$ or —$(CH_2)_m NR_6COR_7$ wherein $R_4$ is hydrogen or $C_{1-6}$alkyl and $R_5$ is hydrogen, $C_{1-6}$ealkyl, $C_{3-6}$cycloalkyl, $C_{6-12}$aryl, $C_{6-12}$aryl$C_{1-6}$alkyl or a $C_{3-9}$heterocyclic group (where the alkyl, aryl or heterocyclic moiety may be optionally substituted by one or more substituents selected from halogen, $C_{1-6}$alkyl, $C_{3-6}$cycloalkyl, $C_{1-6}$alkoxy and $C_{2-6}$alkenyl), or $R_4$ and $R_5$ together with the nitrogen atom to which they are attached form a 4–10-membered heterocyclic group (optionally substituted by one or more substituents selected from halogen, $C_{1-6}$alkyl, $C_{3-6}$cycloalkyl, $C_{1-6}$alkoxy and $C_{2-6}$alkenyl), $R_6$ is hydrogen or $C_{1-6}$alkyl, $R_7$ is $C_{3-6}$cycloalkyl, $C_{3-6}$cycloalkyl-$C_{1-6}$alkyl, $C_{6-12}$aryl, $C_{6-12}$aryl$C_{1-6}$alkyl or a $C_{3-9}$heterocyclic group (where the alkyl, aryl heterocyclic moiety may be optionally substituted by one or more substituents selected from halogen, $C_{1-6}$alkyl, $C_{3-6}$cycloalkyl, $C_{1-6}$alkoxy and $C_{2-6}$alkenyl), X is a bond, $C_{6-12}$aryl or a 5- or 6-membered heteroaryl (where the aryl or heteroaryl moiety is optionally substituted by one or more substituents selected from halogen, $C_{1-6}$alkyl, $C_{3-6}$cycloalkyl, $C_{1-6}$alkoxy and $C_{2-6}$alkenyl);
- wherein m is an integer 1, 2, 3 or 4;
- or a pharmaceutically acceptable salt or solvate thereof.

As used herein the term alkyl means a straight or branched chain alkyl group. Such alkyl groups include methyl, ethyl, i-propyl, n-propyl, n-butyl, s-butyl, t-butyl, n-pentyl, isopentyl, neopentyl, n-hexyl, isohexyl and neohexyl. Such alkyl groups are preferably $C_{1-4}$alkyl. Reference to cycloalkyl includes cyclopropyl and cyclopentyl.

References to alkenyl groups include groups which may be in the E- or Z-form or a mixture thereof and which when they contain at least three carbon atoms, may be branched. Such alkenyl groups are preferably $C_{2-4}$alkenyl Examples of particular alkenyl groups include vinyl, allyl, isopropenyl, butenyl, isobutenyl, pentenyl, isopentenyl, hexenyl, isohexenyl and neohexenyl.

The term halogen includes chloro, bromo, fluoro and iodo.

As used herein the term aryl as a group or part of a group means $C_{6-12}$aryl aromatic groups and includes one or two $C_6$ aromatic rings. Examples of such groups include phenyl, naphthyl, and biphenyl, in particular phenyl.

As used herein the term $C_{3-9}$heterocyclic group means aromatic, saturated and partially saturated $C_{3-9}$heterocyclic groups. It includes one or two $C_{3-5}$ aromatic, saturated or partially saturated rings containing one or more (for example, one to three) heteroatoms selected from oxygen, sulphur, and nitrogen. Examples of such aromatic groups include thienyl, pyridyl, pyrryl, thiazolyl, furanyl, quinolyl and isoquinolyl. Examples of unsaturated groups include piperidinyl pyrrolidinyl and azetidinyl.

The term 5- or 6-membered heteroaryl means a 5- or 6-membered aromatic ring containing one or more (for example, one to three, preferably one) heteroatoms selected from oxygen, sulphur, and nitrogen. For example, thienyl, pyridyl, pyrryl, thiazolyl and furanyl.

The term 4–10 membered heterocyclic ring means an aromatic, saturated or partially saturated 4, 5, 6, 7, 8, 9 or 10 membered ring containing one or more (for example, one to three, preferably one) heteroatoms selected from oxygen, sulphur, and nitrogen. Examples of such aromatic groups include thienyl, pyridyl, pyrryl, thiazolyl, furanyl, quinolyl and isoquinolyl. Examples of unsaturated groups include piperidinyl, pyrrolidinyl and azetidinyl.

The benzothienyl, benzofuranyl, naphthyl, substituted-thienyl and substituted-furanyl moieties include 2- and 3-benzothienyl, 2- and 3-benzofuranyl, 2- and 3-naphthyl, substituted-2-thienyl, substituted-3-thienyl, substituted-2-furanyl and substituted-3-furanyl groups. The benzothienyl, benzofuranyl, naphthyl, thienyl and furanyl ring substituent(s) may be in any one of the available positions. Specific examples of ring substituents include fluoro, chloro and methoxy.

The present invention further includes the compounds of formula (I) or a pharmaceutically acceptable salt or solvate thereof wherein:

(i) $R_1$ is benzothienyl or substituted-thienyl (where the thienyl moiety substituent is $C_{1-6}$alkyl, for example, methyl and ethyl);

(ii) $R_2$ is a substituted-phenyl (where the phenyl moiety substituent is a halogen, for example, fluoro);

(iii) $R_3$ is —$(CH_2)_m XCONR_4R_5$ wherein $R_4$ and $R_5$ together with the nitrogen atom to which they are attached form a 4, 5 or 6-membered heterocyclic group, for example, piperidine, pyrrolidine and azetidine, X is a bond or a $C_6$aryl, for example, phenyl, and m is an integer 1, 2, 3 or 4, in particular 1 or 4;

(iv) $R_3$ is —$(CH_2)_m NR_6 COR_7$ wherein $R_6$ is hydrogen, $R_7$ is $C_{3-6}$cycloalkyl, for example cyclopropyl, $C_{3-6}$cycloalkyl$C_{1-6}$alkyl, for example, cyclopentylmethyl, $C_6$aryl, optionally substituted by one or more $C_{1-6}$alkyl groups, for example phenyl optionally substituted by methyl, m is an integer 1, 2, 3 or 4, in particular 2, 3 or 4;

(v) $R_1$, $R_2$ and $R_3$ are as defined in points (i) to (iv) above;

Further examples of compounds of formula (I) above include the compounds described in Examples 2 and 3.

Preferred compounds according to the present invention include compounds of formula (I) wherein X is $C_{6-12}$aryl or a 5- or 6-membered heteroaryl (where the aryl or heteroaryl moiety is optionally substituted by one or more substituents selected from halogen, $C_{1-6}$alkyl, $C_{3-6}$cycloalkyl, $C_{1-6}$alkoxy and $C_{2-6}$alkenyl); or a pharmaceutically acceptable salt or solvate thereof Particularly preferred compounds according to the invention are:

1-[4-[4-[(4-fluorophenyl)(4-methylthien-2-yl)methylene] piperidin-1-yl]-1-oxobutyl]-piperidine (1:1) ethanedicarboxylate;

1-[4-[4-[(4-fluorophenyl)(4-methylthien-2-yl)methylene] piperidin-1-yl]-1-oxobutyl]-pyrrolidine. dihydrochloride;

1-[4-[4-[(3-fluorophenyl)(4-methylthien-2-yl)methylene] piperidin-1-yl]-1-oxobutyl]-piperidine. hydrochloride;

1-[3-[4-[(4-fluorophenyl)(4-methylthien-2-yl)methylene] piperidin-1-ylmethyl]benzoyl]piperidine;

1-[3-[4-[(4-fluorophenyl)(4-methylthien-2-yl)methylene] piperidin-1-ylmethyl]benzoyl]pyrrolidine.hydrochloride;

1-[3-[4-[(4-fluorophenyl)(benzothien-2-yl)methylene] piperidin-1-ylmethyl]benzoyl]piperidine.maleate;

1-[3-[4-[(4-fluorophenyl)(benzothien-2-yl)methylene] piperidin-1-ylmethyl]benzoyl]pyrrolidine.maleate;

1-[3-[4-[(4-fluorophenyl)(4-ethylthien-2-yl)methylene] piperidin-1-ylmethyl]benzoyl]piperidine.fumarate;

1-[3-[4-[(4-fluorophenyl)(4-ethylthien-2-yl)methylene] piperidin-1-ylmethyl]benzoyl]pyrrolidine.bis hydrochloride;

4,4-dimethyl-1-[3-[4-[(4-fluorophenyl)(4-methylthien-2-yl) methylene]-piperidin-1-ylmethyl]benzoyl] azetidine.maleate;

and pharmaceutically acceptable salts and solvates thereof.

For therapeutic use, salts of the compounds of formula (I) are those wherein the counterion is pharmaceutically acceptable. However, salts of acids which are non-pharmaceutically acceptable may also find use, for example, in the preparation or purification of a pharmaceutically acceptable compound. All salts, whether pharmaceutically acceptable or not are included within the ambit of the present invention.

Examples of pharmaceutically acceptable acid addition salts include those derived from mineral acids such as hydrochloric, hydrobromic, hydroiodic, phosphoric, metaphosphoric, nitric and sulphuric acids, and organic acids, such as tartaric, acetic, trifluoroacetic, citric, malic, lactic, maleic, malonic, fumaric, benzoic, ascorbic, propionic, glycolic, gluconic, succinic and methanesulphonic and arylsulphonic, for example benzene or p-toluenesulphonic acids.

Preferred salts according to the invention include hydrochloric, maleic, succinic and fumaric acid addition salts.

Solvates according to the invention include hydrates.

In a further aspect of the invention there are provided the compounds of formula (I) and their pharmaceutically acceptable salts and solvates for use in therapy, more particularly in the treatment or prophylaxis of psychotic disorders such as schizophrenia, mania, hyperactivity, substance abuse, emesis and schizophreniaform disorders.

The present invention further includes a method for the treatment of an animal, for example, a mammal including a human, suffering from or liable to suffer from a psychotic disorder, including any of the aforementioned disorders, which comprises administering an effective amount of a compound of formula (I) or a pharmaceutically acceptable salt or solvate thereof.

In yet a further aspect, the present invention provides the use of a compound of formula (I) or a pharmaceutically acceptable salt or solvate thereof in the manufacture of a medicament for the treatment or prophylaxis of any of the aforementioned disorders.

The amount of a compound of formula (I) or a pharmaceutically acceptable salt or solvate, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 25 mg per kilogram body weight of the recipient (e.g. a human) per day, preferably in the range of 0.1 to 10 mg per kilogram body weight per day and most preferably in the range 0.25 to 5 mg per kilogram body weight per day. The desired dose may be presented as one, two, three, four, five or more sub-doses administered at appropriate intervals throughout the day.

While it is possible for the active ingredient to be administered alone, it is preferable to present it as a pharmaceutical formulation. Accordingly, the present invention further provides a pharmaceutical formulation comprising a compound of formula (I) or a pharmaceutically acceptable salt or solvate thereof, together with a pharmaceutically acceptable carrier thereof and optionally other therapeutic agents. The carrier must be "acceptable" in the sense of being compatible with the other ingredients of the formulation and not deleterious to the recipients thereof.

Formulations include those suitable for oral, rectal, nasal, topical (including transdermal, buccal and sublingual), vaginal or parenteral (including subcutaneous, intramuscular, intravenous, intradermal and intravitreal) administration. The formulations may be prepared by any methods well known in the art of pharmacy, for example, using methods such as those described in Gennaro et al., Remington's Pharmaceutical Sciences (18th ed., Mack Publishing company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as pills, tablets or capsules each containing a predetermined amount of active ingredient; as a powder or granules; as a solution or suspension. The active ingredient may also be presented as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The present invention further includes the following processes for the preparation of compounds of formula(I).

The compounds of formula (I) may be produced by various methods known in the art of organic chemistry chemistry in general. Starting materials are either known and readily available from chemical sources or may themselves be produced by conventional techniques. For example, the compounds may be synthesised using methods described in *The Chemistry of Heterocyclic Compounds,* vol 44 "Thiophene and its derivatives", parts 1–5, Ed S. Gronowitz J. Wiley and Sons, and A. R. Katritsky and C. W. Rees, *Comprehensive Heterocyclic Chemistry,* Part 4 Ed C. W. Bird and G. H. Cheesman, Pergamon Press.

For example, compounds of formula (I) may be prepared by methods analogous to those disclosed in U.S. Pat. No. 4,540,780.

In the following description the symbols $R_1$, $R_2$, $R_3$, $R_4$, $R_5$, $R_6$, $R_7$, X and m have the meanings ascribed to them in formula (I) unless otherwise stated.

Compounds of formula (I) may be prepared by reacting a compound of formula (II)

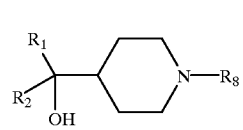

(II)

with a compound of formula $R_3$-L wherein L is a suitable leaving group, such as halogen, for example, chloro, bromo or iodo or methanesulphonyl (mesyl) or toluenesulphonyl (tosyl). The reaction may conveniently be carried out in the presence of a solvent such as toluene or ethanol at a temperature in the range of 60–110° C.

Typically, a compound of formula (II) is reacted with an agent such as 1-(3-halomethylbenzoyl)piperidine, 1-(3-halomethylbenzoyl)pyrrolidine, (4-halo-1-oxobutyl)piperidine (where halo includes chloro, bromo or iodo) or the corresponding mesyl or tosyl derivatives such as (4-mesyloxy-1-oxo-butyl)piperidine, in toluene or ethanol in the presence of a acid scavenger such as triethylamine or potassium carbonate, conveniently at room temperature or at higher temperature up to reflux.

Alternatively, compounds of formula (I) may be prepared from an amine of formula (III)

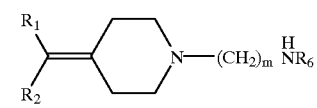

(III)

by acylation. For example, by reacting a compound of formula (III) with the appropriate acid chloride of formula $R_7COCl$.

Amines of formula (III) wherein $R_6$ is an alkyl group may be prepared by alkylation of the corresponding compound of formula (III) wherein $R_6$ is hydrogen using methods known in the chemical literature, for example, with ethyl iodide or methylated by pyrolysis of the formic acid salt prior to acylation, or using reductive alkylation methods.

Where necessary or desired, following one of the above processes, any one or more of the following further steps in any order may be performed:

(i) converting a pharmaceutically acceptable salt or solvate of a compound of formula (I) into a compound of formula (I).

(ii) converting a pharmaceutically acceptable salt or solvate of a compound of formula (I) into another pharmaceutically acceptable salt or solvate of formula (I).

(iii) converting a compound of formula (I) into a pharmaceutically acceptable salt or solvate of a compound of formula (I)

Compounds of formula (II) may conveniently be prepared by dehydration of a compound of formula (IV)

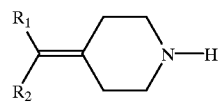

(IV)

wherein $R_8$ is hydrogen or a nitrogen protecting group, such as trityl. Dehydration is typically carried out using a mineral acid such as hydrochloric acid or by using phosphorus oxychloride. The reaction may be conveniently carried out using standard conditions for dehydration of an alcohol. For example, by use of phosphorus oxychloride in the presence of a suitable solvent such as pyridine at a temperature in the range of 80 to 120° C.

Other methods well known to a skilled person or readily available from the chemical literature may be used for the dehydration, including sulphuric acid, 4-methylbenzenesulphonic acid, trifluoroacetic acid, methanesulphonic acid, trifluoromethanesulphonic acid, thionyl chloride, or by use of Martin sulphurane dehydrating agent, employing, where necessary the appropriate solvent.

Compounds of formula (IV) supra wherein $R_6$ is a nitrogen protecting group, for example, trityl may, using methods well known to a skilled person or readily available from the chemical literature, be either simultaneous or sequential dehydrated and deprotected to form a compound of formula (II)

Compounds of formula (IV) may be prepared by treating compounds of formula (V)

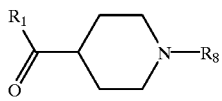

(V)

wherein $R_8$ is hydrogen or a nitrogen protecting group, with an appropriate organometallic reagent, such as a Grignard, or a lithium reagent derived from $R_2$-L in which L is an appropriate halogen, such as bromo or chloro, or a lithio reagent derived from an activated aryl hydrogen atom. For example, compounds of formula (IV) wherein $R_2$ is a phenyl group substituted with a halo atom may conveniently be prepared by treating a compound of formula (V) with the appropriate halo substituted phenyl magnesium halide using standard reaction conditions.

Compounds of formula (IV) may also be prepared by treating compounds of formula (VI)

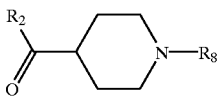

(VI)

wherein $R_8$ is hydrogen or a nitrogen protecting group, with an appropriate organometallic reagent, such as a Grignard, or a lithium reagent derived from $R_1$-L in which L is an appropriate halogen, such as bromo or chloro, or a lithio reagent derived from an activated aryl hydrogen atom. The reaction is typically carried out in the presence of an apolar aprotic solvent such as ether or tetrahydrofuran at a temperature in the range of −60 to 67° C.

Compounds of formula (V) may be prepared by methods known in the chemical literature. For example, compounds wherein $R_1$ is 4-chloro- or 2,3-dichloro-thienyl may be prepared, for example, as described in example 1 by chlorination of the appropriately substituted halobenzoylthiophene. These compounds are commercially available or are prepared using methods known in the art, for example, by Friedal-Crafts benzoylation of the thiophene or other groups represented by $R_1$.

Compounds of formulae (V) and (VI) may, for example, be prepared by the addition of the appropriate Grignard reagent to ethyl N-methyl or N-trityl isnicotinate. The latter compounds are commercially available or may be prepared from commercially available compounds using methods known in the art.

Alternatively, compounds of formula (VI) wherein $R_8$ is acyl or hydrogen and $R_2$ is 4-fluoro-phenyl may be prepared by methods described in J. Med. Chem., 1970, 13, 1. Compounds of formula (V) wherein $R_8$ is trityl may be prepared from compounds of formula (V) wherein $R_8$ is hydrogen, for example by reaction with trityl bromide using the method described in example 4 infra. Compounds of formula $R_3$-L supra may, for example, be prepared by reacting the appropriate carbonylchloride with a suitable amine using methods known to a skilled person.

Compounds of formula (III) supra may be prepared by reacting a compound of formula (II) with the appropriate haloalkyphthalimides, followed by treatment of the intermediate N-alkylphthalimide with hydrazine using methods known in the art.

In the alternative, compounds of formula (III) wherein m is 2 and $R_6$ is hydrogen may be prepared, for example, by treating compounds of formula (II) with bromoacetonitrile in the presence of potassium carbonate and acetonitrile or DMF. This intermediate is subsequently reduced using reagents suitable for the reduction of nitriles to amines. Suitable reducing agents include hydrides such as lithium aluminium hydride.

Salts according to the present invention may be prepared by treating a compound of formula (I) with an appropriate base, for example an alkali metal, alkaline earth metal or ammonium hydroxide, or an appropriate organic or inorganic acid, such as hydrochloric, fumaric or maleic acid.

The present invention further includes all novel intermediates described herein and in particular compounds of formula (II).

The following examples are intended for illustration only and are not intended to limit the scope of the invention in any way.

EXAMPLE 1

4-[(4-fluorophenyl)(4-methylthien-2-yl)methylene]piperidine hydrochloride

To a stirred solution of 4-(1-acetylpiperidinyl) carbonylchloride (50 g) in dichloromethane (690 ml), under a nitrogen atmosphere, at −25° C., was sequentially added powdered aluminium chloride (71 g) followed by a solution of 2-bromo-3-methylthiophene (50 g) in dichloromethane (300 ml) over 17 min. After 30 min. water (240 ml) was added dropwise to the reaction whilst allowing the reaction temperature to rise to about +20° C. After stirring for a further 30 min the inorganic components were removed by filtration through a pad of dicalite. The layers were separated, the organic layer was washed twice with water, dried ($Na_2SO_4$) and evaporated under reduced pressure. The crude product (73 g) was purified by chromatography to yield 2-(5-bromo4-methylthienyl)-4-(1-acetylpiperidine)methanone (62.2 g); mp 105–108.5° C. (decomp).

A suspension of zinc dust (22 g), sodium iodide (11 g), triphenylphosphine (16.5 g) and nickel chloride hexahydrate (2.56 g) in deoxygenated methanol (340 ml) (prepared by boiling methanol in a stream of nitrogen for 2 h), was stirred in a nitrogen atmosphere at 60° C. for 15 min. To this mixture was added a solution of the above bromo compound (62.2 g) in deoxygenated methanol (150 ml) and the reaction was boiled under reflux in a nitrogen atmosphere for 22 h. The reaction was cooled and the inorganic components were removed by filtration through a pad of dicalite. The filtrate was evaporated and the residue was dissolved in dichloromethane. The solution was washed with dilute mineral acid, followed by water to neutrality, dried ($Na_2SO_4$) and evaporated to dryness under reduced pressure. The crude product (61.3 g) was purified by flash chromatography and crystallised from dichloromethane/ether to give, in two crops, 2-(4-methylthienyl)-4-(1-acetylpiperidine)methanone (41.2 g); m.p. 120–125° C. A solution of this methanone (41.2 g) in 5N aqueous hydrochloric acid (140 ml) was boiled under reflux for 16 h then evaporated under reduced pressure, azeotroping the remaining water with toluene. Trituration of the residue with diethyl ether gave the crude product (38.8 g) which was isolated by filtration. Recrystallisation from a mixture of methanol and diethyl ether gave 2-(4-methylthienyl)-4-piperidinemethanone hydrochloride in two crops (29.5 g); m.p. 217.5–218.5° C. (change in crystal form above 200° C.).

A solution of the above hydrochloride (28 g) in water was basified and a solution of this (24.1 g) in dichloromethane (240 ml) and triethylamine (48 ml) was stirred at 0° C. under a nitrogen atmosphere. Triphenylmethyl chloride (33.7 g)

was added in portions, at such a rate to maintain the reaction temperature at 0±2° C. After 30 min the mixture was cautiously diluted with water (240 ml) and extracted into dichloromethane. The extract was washed, dried (Na$_2$SO$_4$) and evaporated under reduced pressure, partially replacing the dichloromethane with heptane, and allowed to crystallise. The crystals were filtered and washed with a 4:1 mixture of heptane and dichloromethane to yield 2-(4-methylthienyl)-4-(1-triphenylmethylpiperidine)-methanone (46.9 g); mp 219–221° C. (decomp).

Bromoethane (1.5 ml) was added to a stirred suspension of magnesium turnings (6.4 g) in dry diethyl ether (100 ml) containing a crystal of iodine.

The exothermic reaction was maintained at 32 to 36° C. throughout whilst a solution of 4-bromofluorobenzene (29 ml) in dry diethyl ether (170 ml) was cautiously added. The resulting mixture was gently boiled under reflux for 30 min then cooled to 0° C. To this mixture was added dropwise, over 15 min., a solution of the above methanone (23.5 g) in dry diethyl ether (280 ml) while maintaining the temperature between 0 and 5° C. The reaction was then allowed to warm to room temperature over 30 min and the product was extracted with ethyl acetate. The extracts were washed with water, dried (Na$_2$SO$_4$) and evaporated under reduced pressure to yield a gum (32.4 g) which was dissolved in a mixture of acetic acid (261 ml) and water (130 ml)) and the solution was boiled under reflux for 18 h. Water (130 ml) was added and the reaction was cooled to <5° C. Solid material (triphenylmethyl alcohol) was filtered off and the filtrate was evaporated under reduced pressure to a low volume. The residue was basified with concentrated ammonium hydroxide solution and the product was extracted into ethyl acetate. The extract was washed with aqueous sodium chloride solution, dried (Na$_2$SO$_4$) and evaporated to dryness under reduced pressure to yield a gummy residue (15.0 g). A solution of hydrogen chloride in methanol was added to a solution of this material in diethyl ether and the solution was allowed to crystallise to give 4-[(4-fluorophenyl)(4-methylthien-2-yl)methylene]piperidine hydrochloride (9.0 g); mp 191–206° C. (decomp).

EXAMPLE 2

1-[3-[4-[(4-fluorophenyl)(4-methylthien-2-yl)methylene]piperidin-1-ylmethyl]benzoyl]piperidine.
(2a)

3-Chloromethylbenzoyl chloride (1.45 ml) was added to a solution of piperidine (1 ml) in triethylamine (2 ml) and the mixture was stirred under nitrogen at 5° C. for 45 min. Water was added, the product was extracted with dichloromethane and the extract was washed with water, dried over sodium sulphate and evaporated to give 1(3-chloromethylbenzoyl) piperidine (2.32 g) as an oil.

A solution of this benzoyl piperidine (2.3 9), the above 4-[(4-fluorophenyl)(4-methylthien-2-yl)methylene] piperidine (3 g) and triethylamine (3 ml) in toluene was boiled under reflux for 5 h. Water was added to the cooled mixture, the layers were separated and the toluene layer was separated, washed with brine, dried over sodium sulphate and evaporated. The resultant oil (5.6 g) was dissolved in dichloromethane and chromatographed on silica. Elution with dichloromethane/ammonium hydroxide (1%) containing increasing amounts of methanol gave fractions that on evaporation gave the title compound (4.36 g). A solution of this compound in ether was treated with with an ethereal solution of hydrogen chloride. The precipitate was collected and dried to give the hydrochloride salt (3.6 g) m.p. 118–142° C.

The following compounds were prepared in a similar manner using the appropriate chloroalkylacid chloride:

2b: 1-[3-[4-[(4fluorophenyl)(4-methylthien-2-yl) methylene]piperidin-1-ylmethyl]benzoyl] pyrrolidine.hydrochloride m.p. 118–127° C.

2c: 1-[4-[4-[(4-fluorophenyl)(4-ethylthien-2-yl)methylene] piperidin-1-yl]-1-oxo-butyl]-piperidine.dihydrochloride, m/e, 454

2d: 1-[4-[4-[(4-fluorophenyl)(4-ethylthien-2-yl)methylene] piperidin-1-yl]-1-oxo-butyl]-pyrrolidine bis-hydrochloride m.p 167.4° C.

2e: 1-[4-[4-[(4-fluorophenyl)(benzothien-2-yl)methylene] piperidin-1-yl]-1-oxo-butyl]piperidine.dihydrochloride m.p. 117–121° C.

2f: 1-[4-[4-[(4-fluorophenyl)(benzothien-2-yl)methylene] piperidin-1-yl]-1-oxo-butyl]pyrrolidine maleate; m/e, 462

2g: 1-[3-[4-[(4-fluorophenyl)(benzothien-2-yl)methylene] piperidin-1-ylmethyl]-benzoyl]piperidine.maleate m.p. 179–183° C.

2h: 1-[3-[4-[(4-fluorophenyl)(benzothien-2-yl)methylene] piperidin-1-ylmethyl]-benzoyl]pyrrolidine.maleate m.p.157–163° C.

2i: 1-[3-[4-[(4-fluorophenyl)(4-ethylthien-2-yl)methylene] piperidin-1-ylmethyl]-benzoyl]piperidine.fumarate m.p.173.4° C.

2j: 1-[3-[4-[(4-fluorophenyl)(4-ethylthien-2-yl)methylene] piperidin-1-ylmethyl]-benzoyl] pyrrolidine.dihydrochloride m.p. 167.4° C.

2k: 4,4-dimethyl-1-[3-[4-[(4-fluoropheny)(4-methylthien-2-yl)methylene]piperidin-1-ylmethyl]benzoyl] azetidine.maleate m.p. 173.7° C.

2l: 1-[4-[4-[(4-fluorophenyl)(4-methylthien-2-yl) methylene]piperidin-1-yl]-1-oxobutyl]-piperidine (1:1) ethanedicarboxylate m.p. 172–174° C.

2m: 1-[4-[4-[(4-fluorophenyl)(4-methylthien-2-yl) methylene]piperidin-1-yl]-1-oxobutyl]-pyrrolidine.dihydrochloride m.p. 144–146° C.

2n: 1-[4-[4-[(3-fluorophenyl)(4-methylthien-2-yl) methylene]piperidin-1-yl]-1-oxobutyl]-piperidine.hydrochloride m.p. 148–154° C.

EXAMPLE 3

Preparation of N-[-4-[4-[(4-fluorophenyl)(4-methylthien-2-yl)methylene]-piperidin-1-ylbutyl] benzamide.oxalate (3a)

A solution of 4-[(4-fluorophenyl)(4-methylthien-2-yl) methylene]piperidine (2 g), 4-bromobutylphthalimide (1.76 g), and triethylamine (2 ml) in toluene (20 ml) was boiled under reflux for 4 h. The solution was cooled, diluted with water, and the toluene layer was separated and evaporated to give the phthalimide as a dark oil 3. g) which was puified as the oxalate salt. A solution of the foregoing phthalimide (1.88 g) and hydrazine hydrate (0.37 ml) in ethanol (20 ml) was boiled at reflux for 2 h. The ehanol was removed by evaporation at reduced pessure and water and sodium carbonate were added. The product was extracted with dichloromethane, the extract was washed with water, dried and evaporated to give 1-(4-aminobutyl)4-[(4-fluorophenyl) (4-methylthien-2-yl)methylene]piperidine as an oil (1.16 g). Benzoyl chloride was added to a solution of the foregoing amine in dichloromethane, containing triethylamine (1 ml), and the solution was stirred at room temperature for 2 h. Water and further dichloromethane were added to the solution, the layers ere separated and the dichloromethane layer was dried and evaporated to give a dark gum (1.56 g).

This material was chromatographed on silica, eluting with dichloromethane containing increasing amounts of methanol, and converted to the oxalate salt which was crystallised from methanol/ether to give the title compound m.p. 95–98° C.

The following compounds were prepared in a similar manner:

3b: N-[3-[4-[(4-fluorophenyl)(4-methylthien-2-yl)methylene]piperidin-1-yl]-propyl]benzamide hydrochloride m.p. 95–97° C.

3c: 4-methyl-N-[2-[4-[(4-fluorophenyl)(4-methylthien-2-yl)methylene]piperidin-1-yl]ethyl]benzamide oxalate m.p. 189–191° C.

3d: 4-methyl-N-[2-[4-[(4-fluorophenyl)(4-methylthien-2-yl)methylene]piperidin-1-yl]ethyl]-N-methylbenzamide m.p. 114–116° C.

3e: N-[2-[4-[(4-fluorophenyl)(4-methylthien-2-yl)methylene]piperidin-1-yl]-ethyl]cyclopropylcarboxamide oxalate m.p. 98–101° C.

3f: N-[2-[4-[(4-fluorophenyl)(4-methylthien-2-yl)methylene]piperidin-1-yl]-ethyl]cyclopentylcarboxamide m.p oxalate. 145–148° C.

EXAMPLE 4

Apomorphine Climbing Test in Mice

The ability of dopamine receptor antagonists to inhibit the behavioural effects in rodents caused by dopamine agonists such as apomorphine is a well established criterion for predicting the antipsychotic efficacy of these drugs in man (see e.g. W. C. Bowman and M. J. Rand, Textbook of Pharmacology, 2nd ed., 1980, 15, 6). A particularly relevant test in this respect is the apomorphine climbing test (ACT) which measures the ability of a dopamine antagonist to inhibit the climbing behaviour in mice, induced by the subcutaneous or oral administration of apomorphine. Activity in this test, following systemic and oral administration, has been widely used as a predictor of antipsychotic activity i.e. anti-schizophrenic activity (see e.g. J. T Strupczewski et.al., *J. Med. Chem.*, 1995, 38, 1119). Mice treated with apomorphine HCl tend to adopt a vertical position along the wall of a wire mesh cylinder, standing or climbing. This climbing behaviour is considered to be elicited by apomorphine-mediated stimulation of dopamine receptors. Many drugs affect the climbing behaviour, but dopamine antagonists generally inhibit it in doses not interfering with spontaneous motor activity and/or motor coordination in mice. Test compounds which modulate this climbing behaviour may have antipsychotic activity. The various treatments are randomly distributed over the mice. Each experiment consists of 1+n treatment groups: 1 being a control group of 12 mice receiving apomorphine and vehicle subcutaneously or being a control group of 12 mice receiving apomorphine subcutaneously and vehicle orally; n being (usually 4) compound groups of 12 mice receiving apomorphine and test compound subcutaneously or being compound groups of 12 mice receiving apomorphine subcutaneously and test compound orally.

Experiments are performed in 3 runs of 20 mice each. The mice are marked and weighed, test compound or vehicle is administered subcutaneously and the mice are placed in small Macrolon cages of 17×11×13 cm, 5 mice per cage, or test compound or vehicle is administered orally and the mice are placed in Macrolon cages of 29×11×3 cm, 5 mice per cage. After 30 min 0.75 mg/kg apomorphine HCl is administered subcutaneously in mice treated subcutaneously with vehicle or test compound, or 0.75 mg/kg apomorphine HCl is administered subcutaneously in mice treated orally with vehicle or test compound, and the mice are placed individually in a wire mesh cylinder (diameter 12 cm, height 14 cm).

At 10 min after the treatment with apomorphine the climbing behaviour of each mouse is observed and expressed as a score, according to the following grade:

| | |
|---|---|
| 4 paws on the floor | score 0 |
| 1 or 2 paws holding the wall | score 1 |
| 3 or 4 paws holding the wall | score 2 |

At 20 min after the treatment with apomorphine the climbing behaviour is observed and scored again. For each treatment group the mean score per mouse is determined. The score of the control group should be at least 1.0; if not, the trial is rejected. The final result per group is expressed as the percentage over the control group.

The results of this test for the present test compounds are denoted in Table I (subcutaneous administration of test compound).

TABLE I

| Compound No. | ACT($ED_{50}$) mg/kg |
|---|---|
| Compound 2l | s.c. |
| | 0.3 |
| Compound 2m | 0.14 |
| Compound 2n | 0.34 |

2l = 1-[4-[4-[(4-fluorophenyl)(4-methylthien-2-yl)methylene]piperidin-1-yl]-1-oxobutyl]-piperidine (1:1) ethanedicarboxylate
2m = 1-[4-[4-[(4-fluorophenyl)(4-methylthien-2-yl)methylene]piperidin-1-yl]-1-oxobutyl]-pyrrolidine. dihydrochloride
2n = 1-[4-[4-[(3-fluorophenyl)(4-methylthien-2-yl)methylene]piperidin-1-yl]-1-oxobutyl]-piperidine. hydrochloride

EXAMPLE 5

Catalepsy in Rats

Male Wistar rats (100–125 g, Olac UK) were used for catalepsy experiments. Catalepsy was assessed as described previously (Broekkamp et al, *Naunyn-Schmiedeberg's Arch. Pharmacol.* 338, 191 1988). Briefly, rats were tested in 6 different observation trials in which the animals were placed in abnormal postures and scored positively with one point for maintaining the imposed posture for 10 s. The imposed postures were: vertical clinging to a grid, upright standing with a high support for the front paws, extension of hindlegs, placement on back, placement of spatula in the mouth and rotation in a wire mesh cylinder.

Theoretically a maximum score of 6 can be reached. Catalepsy was assessed at 60 and 120 minutes after drug administration. The data were evaluated by 2 way ANOVAR followed by a Newman Kools post hoc test and $ED_{50}$ values calculated (Table II).

TABLE II

| Compound No | CATR ($ED_{50}$) mg/kg |
|---|---|
| 2m | >7 mg/kg |
| 2n | >17 mg/kg |

What is claimed is:

1. A compound of the formula (I)

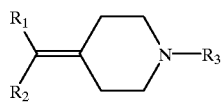

wherein R₁ is benzothienyl, benzofuranyl, naphthyl, substituted-thienyl or substituted-furanyl, wherein the benzothienyl, benzofuranyl or naphthyl moiety is unsubstituted or substituted by one or more substituents selected from halogen, $C_{1-6}$-alkyl, $C_{3-6}$-cycloalkyl, $C_{1-6}$-alkoxy and $C_{2-6}$-alkenyl and wherein the thienyl or furanyl moiety is substituted by one or more substituents selected from halogen, $C_{1-6}$-alkyl, $C_{3-6}$-cycloalkyl, $C_{1-6}$-alkoxy and $C_{2-6}$-alkenyl;

R₂ is substituted-phenyl or substituted-thienyl, wherein the phenyl or thienyl moiety is substituted by one or more substitutents selected from $C_{1-6}$-alkyl and halogen;

R₃ is —(CH₂)ₘXCONR₄R₅;

R₄ and R₅ together with the nitrogen atom to which they are attached form a 4- or 5-membered heterocyclic ring that is unsubstituted or substituted by one or more substituents selected from halogen, $C_{1-6}$-alkyl, $C_{1-6}$-cycloalkyl, $C_{1-6}$-alkoxy and $C_{2-6}$-alkenyl;

X is a bond;

m is the integer 1, 2, 3 or 4;

or a pharmaceutically acceptable salt thereof or a solvate thereof.

2. The compound according to claim 1, wherein R₁ is benzothienyl or substituted-thienyl, wherein the thienyl moiety substituent is $C_{1-6}$-alkyl, or a pharmaceutically acceptable salt or solvate thereof.

3. The compound according to claim 1, wherein R₂ is substituted-phenyl, and the phenyl moiety substituent is halogen, or a pharmaceutically acceptable salt or solvate thereof.

4. A pharmaceutical formulation comprising the compound of claim 1 or a pharmaceutically acceptable salt or solvate thereof together with a pharmaceutically acceptable carrier therefor.

5. The compound according to claim 1 which is 1-[4-[4-[(4-fluorophenyl)(4-methylthien-2-yl)methylene]piperidin-1-yl]-1-oxobutyl]-pyrrolidine dihydrochloride.

6. A pharmaceutical formulation comprising the compound of claim 2 or a pharmaceutically acceptable salt or solvate thereof together with a pharmaceutically acceptable carrier therefor.

7. A pharmaceutical formulation comprising the compound of claim 3 or a pharmaceutically acceptable salt or solvate thereof together with a pharmaceutically acceptable carrier therefor.

8. A pharmaceutical formulation comprising the compound of claim 5 or a pharmaceutically acceptable salt or solvate thereof together with a pharmaceutically acceptable carrier therefor.

9. A process for the preparation of a compound of claim 1 comprising reacting a compound of formula (II)

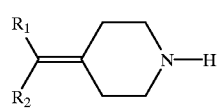

with a compound of the formula R₃-L, wherein R₁, R₂ and R₃ are as defined in claim 1 and L is a suitable leaving group.

* * * * *